US00PP37264P2

(12) United States Plant Patent
Jachertz

(10) Patent No.: US PP37,264 P2
(45) Date of Patent: Feb. 10, 2026

(54) ***HAWORTHIA* PLANT NAMED 'LIZARD KING'**

(50) Latin Name: *Haworthia fasciata*
Varietal Denomination: LIZARD KING

(71) Applicant: Deltacactus S.L., Amposta (ES)

(72) Inventor: Christian Jachertz, Amposta (ES)

(73) Assignee: DeltaCactus S.L. (ES)

( * ) Notice: Subject to any disclaimer, the term of this patent is extended or adjusted under 35 U.S.C. 154(b) by 0 days.

(21) Appl. No.: 19/194,392

(22) Filed: Apr. 30, 2025

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
CPC ..... A01H 5/12; A01H 5/00; A01H 6/00
See application file for complete search history.

(56) References Cited

PUBLICATIONS

Canadian Greenhouse Conference New Variety Showcase, retrieved on Jun. 9, 2025 at https://www.canadiangreenhouseconference.com/attendee-information/new-variety-showcase, 5 pp. (Year: 2025).*
Delta Cactus Loving Succulents 2024, retrieved on Jun. 9, 2025 at https://static.messe-essen-digitalmedia.de/uploads/E501/pdf/company/deltacactus-sl-ed429-info-en.pdf, 12 pp. (Year: 2024).*
Walker, All change in Aloe and Haworthia, Cactus World 2013, vol. 31 (4), 297. (Year: 2013).*

* cited by examiner

*Primary Examiner* — June Hwu

(57) ABSTRACT

A new and distinct cultivar of *Haworthia* plant named 'Lizard King' is disclosed, characterized by rosettes of narrow, slightly elongated foliage. Leaves are densely tuberculate. Tubercles are uniquely off-white in color. The new variety is a *Haworthia*, typically produced as a garden or container plant.

2 Drawing Sheets

Latin name of the genus and species: *Haworthia fasciata.*
Variety denomination: 'LIZARD KING'.

BACKGROUND OF THE INVENTION

The new cultivar is a product of a naturally-occurring whole plant mutation of the unpatented variety *Haworthia* 'Universe'. 'LIZARD KING' was found and selected by the inventor in September 2020 at a nursery in Amposta, Spain.

Asexual reproduction of the new cultivar 'LIZARD KING' was first performed in Amposta, Spain in March 2021, by vegetative cuttings. 'LIZARD KING' has since produced several generations and has shown that the unique features of this cultivar are stable and reproduced true to type.

SUMMARY OF THE INVENTION

The cultivar 'LIZARD KING' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LIZARD KING.' These characteristics in combination distinguish 'LIZARD KING' as a new and distinct *Haworthia* cultivar:

1. Unique leaf texture with tubercles arranged in near horizontal lines on the lower surface.
2. Uniquely off-white colored tubercles.

PARENTAL COMPARISON

Plants of the new cultivar 'LIZARD KING' are similar to the parent variety in most horticultural characteristics. However, plants of the new variety differ from the parent variety in the following:

1. Leaf color of the new variety is lighter green than the leaf color of the parent.
2. Inner leaf tubercles of the new variety are off-white, while the inner leaf lenticel dots of the parent are white.
3. Outer leaf tubercles of the new variety are off-white to white, while the outer leaf lenticel dots of the parent are white.

COMMERCIAL COMPARISONS

'LIZARD KING' can be compared to the unpatented commercial variety *Haworthia attenuata* 'Enon', unpatented. The two varieties are similar in most horticultural characteristics; however, the new variety differs in the following:

1. Leaves of the new variety are longer and more slender than leaves of this comparator.

'LIZARD KING' can be compared to the unpatented commercial variety *Haworthia fasciata* 'Big Band', unpatented. The two varieties are similar in most horticultural characteristics; however, the new variety differs in the following:

1. The tubercles of the new variety are not overlapping on the leaf-downside. The lenticel dots of this comparator are grouped together, thus showing tubercles bands on the leaf-downside.

BRIEF DESCRIPTION OF THE PHOTOGRAPHS

Figure 1:
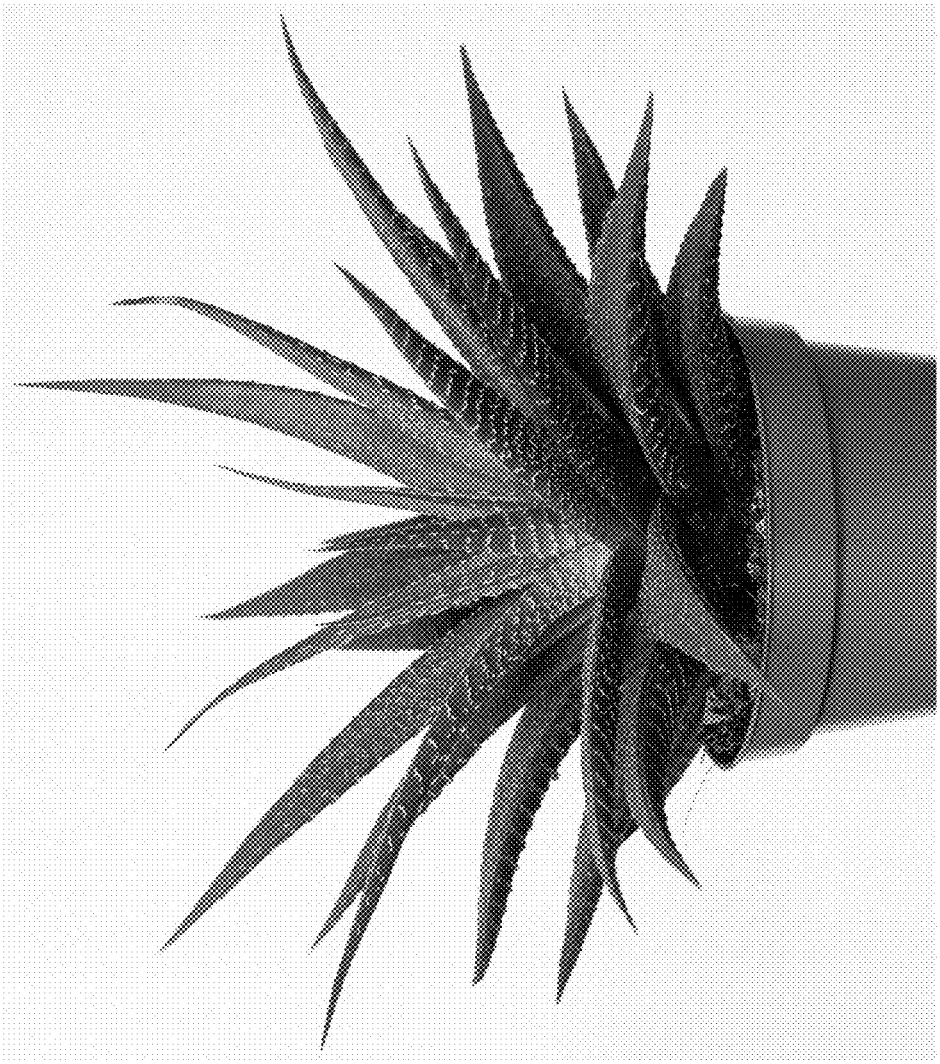
Figure 2:
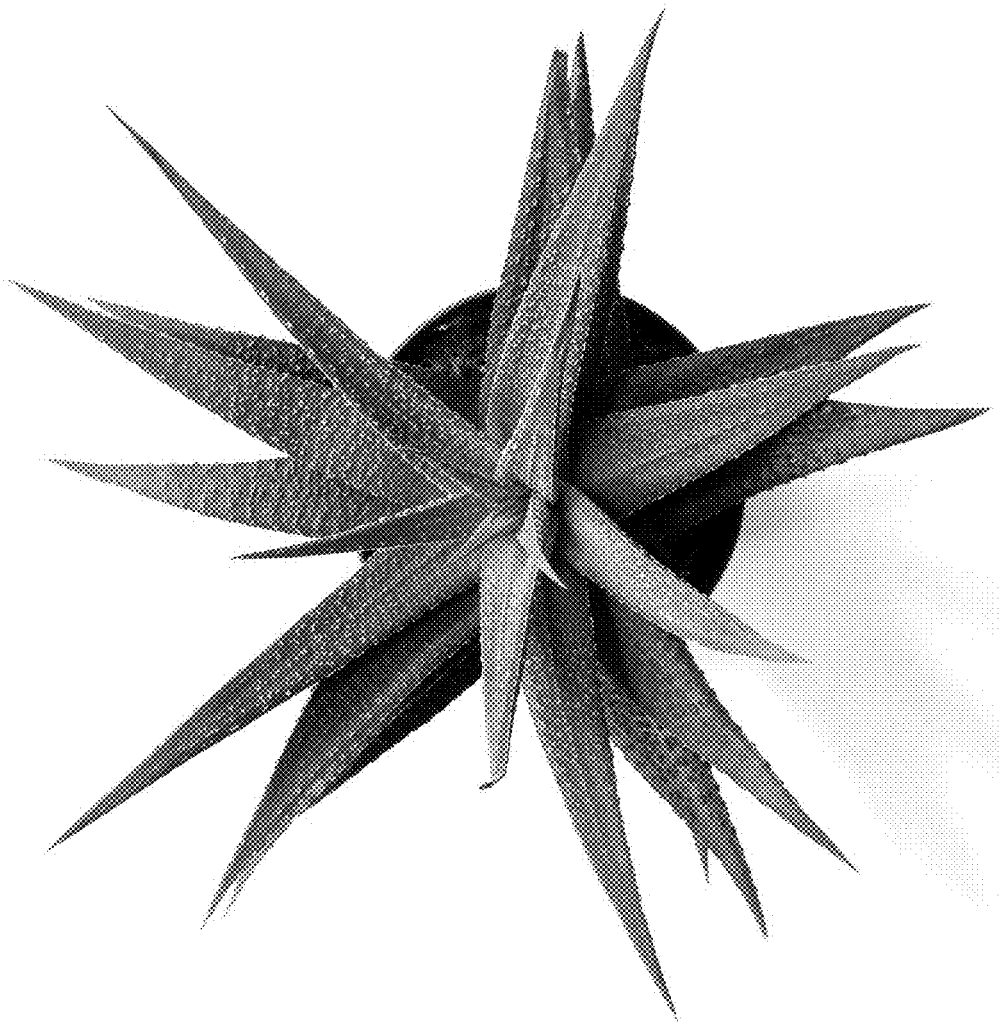

The accompanying photograph in FIG. 1 illustrates in full color a side-view of a typical plant of 'LIZARD KING' grown in a greenhouse in Amposta, Spain. This plant is approximately 6 months old, shown in a 9-centimeter container. FIG. 2 illustrates a top-view of the same plant. The photographs were taken using conventional techniques and although colors may appear different from actual colors due to light reflectance it is as accurate as possible by conventional photographic techniques.

DETAILED BOTANICAL DESCRIPTION

In the following description, color references are made to the Royal Horticultural Society Colour Chart, 2015 edition, except where general terms of ordinary dictionary significance are used. The following observations and measurements describe 'LIZARD KING' plants in a glass greenhouse in Amposta, Spain. Temperatures ranged from 18° C. to 20° C. during the day, and 15° C. to 18° C. during the night. No artificial light, photoperiodic treatments or chemical treatments were given to the plants. Natural light conditions were approximately 2500 to 3000 fc of light. Measurements and numerical values represent averages of typical plant types.

Botanical classification: *Haworthia fasciata* 'LIZARD KING'.

Age of the Plant Described: 6 months.

PROPAGATION

Time to Initiate Roots: Approximately 14 days in summer; 21 days in winter at 20° C.

Time to Produce Rooted Cutting: Approximately 80 days in summer; 90 days in winter at 20° C.

Root Description: Fibrous, fleshy, thick, moderately dense and freely-branching. White in color with yellow tips, not accurately measured with the RHS chart.

Propagation Method: Vegetative cuttings.

PLANT

Plant Type: Perennial potted plant.

Plant Shape: Flattened globular.

Growth Habit: Basal rosette.

Container size: 6 cm pots and larger.

Height: Average 13.3 cm; no flowering observed.

Plant Spread: Average 19.2 cm.

Growth Rate: Moderate.

Vigor: Moderate.

Branching Characteristics: Leaves in basal rosettes; 1 basal rosette per plant.

FOLIAGE

Leaf:

*Arrangement*.—Single rosette.

*Quantity*.—Average 29 leaves per rosette.

*Average Length*.—10.1 cm.

*Average Width*.—2.5 cm.

*Thickness*.—0.7 cm.

*Shape of blade*.—Lanceolate, succulent.

*Whole leaf aspect*.—Leaves in an average angle of 50° to vertical, lamina sightly concave, slightly curved downward.

*Apex*.—Long and narrow acuminate.

*Base*.—Broad cuneate.

*Margin*.—Very finely dentate, average length of teeth: 0.5 mm, average height of teeth: 0.3 mm, colored RHS Greyed-Green 192C and 192D.

*Texture of top surface*.—Densely tuberculate, tubercles_placed randomly on lamina or loosely arranged in axial lines on lamina, following main veins, shaped circular to oblong, average length: 0.6 mm, average width: 0.4 mm, average height: 0.5 mm and less, colored RHS Greyed-Green 192B.

*Texture of bottom surface*.—Densely tuberculate, tubercles forming in radial lines on lamina, average length: 2.0 mm, average width: 0.4 mm, average height: 0.5 mm and less, colored RHS Greyed-Green 192A and 192B.

*Pubescence*.—None.

*Rugosity*.—Both sides non-rugose.

*Luster*.—Upper side: Matte to very slightly glossy. Under side: Matte to very slightly glossy.

*Color*.—Young foliage upper side: RHS Green 137B; fading to Yellow-Green 145B and 145C towards base; tubercles near Green-White 192C and 192D. Young foliage under side: RHS Green 137B and 137C; fading to Yellow-Green 144D and 150D towards base; tubercles near Green-White 157C and 157D. Mature foliage upper side: RHS Green NN137A flushed Yellow-Green 147A; fading to Greyed-Green 197C and 197D towards base; tubercles near Greyed-Green 192B. Mature foliage under side: RHS Green NN137A flushed Yellow-Green 147A; fading to Greyed-Green 197C and 197D towards base; tubercles near Greyed-Green 192A and 192B.

*Venation*.—Pattern: Parallel; not visible.

FLOWER

Flowering not observed to date.

REPRODUCTIVE ORGANS

Not observed to date.

OTHER CHARACTERISTICS

Seeds and fruits: Not observed to date.

Temperature tolerance: Unknown, at least tolerant to temperatures up to 40° C. USDA zone 10 to 12.

Tolerance to wind and rain: Low tolerance to rain; high tolerance to wind.

Disease/pest resistance: Similar to other *Haworthia* varieties.

What is claimed is:

1. A new and distinct cultivar of *Haworthia* plant named 'Lizard King' as herein illustrated and described.

* * * * *